(12) United States Patent
McQueen (10) Patent No.: US 10,139,040 B2
(45) Date of Patent: Nov. 27, 2018

(54) APPARATUS AND METHOD FOR ROTATING CYLINDRICAL MEMBERS

(71) Applicant: Joe C. McQueen, Odessa, TX (US)

(72) Inventor: Joe C. McQueen, Odessa, TX (US)

(*) Notice: Subject to any disclaimer, the term of this patent is extended or adjusted under 35 U.S.C. 154(b) by 619 days.

(21) Appl. No.: 14/687,725

(22) Filed: Apr. 15, 2015

(65) Prior Publication Data

US 2016/0305601 A1 Oct. 20, 2016

(51) Int. Cl.

| | |
|---|---|
| *F16M 11/18* | (2006.01) |
| *G01N 17/00* | (2006.01) |
| *B08B 1/00* | (2006.01) |
| *F16H 1/22* | (2006.01) |
| *F16H 1/02* | (2006.01) |

(52) U.S. Cl.
CPC .............. *F16M 11/18* (2013.01); *B08B 1/00* (2013.01); *F16H 1/02* (2013.01); *F16H 1/22* (2013.01); *G01N 17/00* (2013.01)

(58) Field of Classification Search
CPC .. F16M 11/18; F16H 1/02; F16H 1/22; G01N 17/00; B08B 1/00
See application file for complete search history.

(56) References Cited

U.S. PATENT DOCUMENTS

| | | | |
|---|---|---|---|
| 2,023,381 A | 12/1935 | Hume | |
| 2,135,838 A * | 11/1938 | Paxton | B65G 13/07 198/791 |
| 2,990,600 A | 7/1961 | Trya | |
| 3,164,491 A | 1/1965 | Brockett et al. | |
| 3,523,391 A | 8/1970 | Levinson et al. | |
| 3,708,079 A | 1/1973 | Wloszek | |
| 3,835,587 A | 9/1974 | Hall, Jr. | |
| 3,963,231 A | 6/1976 | Cooper | |
| 4,016,681 A | 4/1977 | Leliaert | |
| 4,213,345 A | 7/1980 | Dufour | |
| 4,222,205 A | 9/1980 | Lake et al. | |
| 4,465,422 A | 8/1984 | Blust, Sr. et al. | |
| 4,704,826 A | 11/1987 | Kirland | |
| 4,704,986 A | 11/1987 | Remp et al. | |
| 5,893,682 A | 4/1999 | Oliveri | |

(Continued)

FOREIGN PATENT DOCUMENTS

| | | |
|---|---|---|
| DE | 0438837 A2 | 7/1991 |
| JP | 2003047981 * | 2/2003 |

OTHER PUBLICATIONS

PCT/ISA/210, International Search Report, Issued by USPTO, dated Jul. 15, 2016.

(Continued)

*Primary Examiner* — John C Hong (57) ABSTRACT

Methods and apparatus, comprising a housing, a first plurality of gears positioned within the housing, a second plurality of gears positioned within the housing, and a plurality of wheels positioned externally of the housing, are usable for rotating cylindrical objects. Each gear of the second plurality of gears is engaged with two gears of the first plurality of gears, and the housing is adapted to contain gear lubricating fluid therein. The plurality of wheels is connected with the first plurality of gears, and each wheel, of the plurality of wheels, has a diameter that is larger than a height of the housing. The plurality of wheels rotates one or more cylindrical objects positioned thereon.

16 Claims, 4 Drawing Sheets

(56) References Cited

U.S. PATENT DOCUMENTS

| | | | |
|---|---|---|---|
| 5,967,064 A | 10/1999 | Keldenich et al. | |
| 6,158,574 A * | 12/2000 | Williams | B65G 13/073 |
| | | | 198/780 |
| 6,354,193 B1 | 3/2002 | Lee | |
| 6,367,618 B1 * | 4/2002 | Szuba | B65G 13/073 |
| | | | 198/781.01 |
| 7,815,032 B2 | 10/2010 | Preston et al. | |
| 8,061,296 B1 | 11/2011 | Batur | |
| 2007/0138112 A1 | 6/2007 | Meyer et al. | |
| 2012/0103319 A1 | 5/2012 | Sheridan | |
| 2013/0104746 A1 | 5/2013 | Hankins | |
| 2013/0220389 A1 | 8/2013 | Snow | |

OTHER PUBLICATIONS

PCT/ISA/237, Written Opinion of the International Searching Authority, Issued by USPTO, dated Jul. 15, 2016.

\* cited by examiner

APPARATUS AND METHOD FOR ROTATING CYLINDRICAL MEMBERS

FIELD

The present invention relates generally to apparatus and methods for rotating cylindrical members, and in particular, but without limitation, to an apparatus and a method for rotating tubulars, pipe, and other cylindrical members as part of a system for coating, cleaning, and/or inspecting internal and/or external surfaces of the tubulars, pipe, and other cylindrical members.

BACKGROUND

Coating, cleaning, and inspecting the inside and the outside of tubulars, pipe, and other cylindrical members (hereinafter collectively referred to as "tubulars"), such as oilfield pipe, are operations well known in the art. For example, abrasion cleaning and coating an inside surface of a tubular with a material applied thereto is used to prevent corrosion and erosion of the inside surface. Additionally, drill pipe is often cleaned and coated in order to reduce friction and wear in the pipe. Pipe that have been coated also require less pressure to pump fluid due to reduced friction.

With recent advances in material science and the demand for deeper and wider wells, downhole pipe lengths and diameters are increasing. The increased pipe lengths have limited the usefulness of previous inventions in this field due to the fact that prior cleaning and coating devices are unable to provide a uniform cleaning action or coating over an extended length. Despite the improvements in cleaning and coating technologies, problems of uneven erosion and coating thickness over the length of pipe have persisted.

Furthermore, a typical cleaning and coating system comprises a tubular rotating station capable of rotating only one or two tubulars simultaneously. With the ever increasing demand for cleaned and/or coated tubulars, such systems are not capable of cleaning and coating large quantities of tubulars. Therefore, there is a need for providing a rotating device that can receive and simultaneously rotate a plurality of tubulars. There is a need in the art for providing a coating device which turns all pipe sections at a constant predetermined speed.

Another drawback of previous tubular rotating devices is that they were unable to receive and rotate tubulars having different diameters. Specifically, the previous devices can receive and rotate a tubular having a specific diameter and cannot adjust for tubulars having smaller or larger diameters. Therefore, there is a need for providing a rotating device that can receive and rotate tubulars of different diameters, simultaneously and/or consecutively.

Yet another drawback of the previous tubular rotating devices is their susceptibility to being contaminated by debris, cleaning agents, and coating particles and agents during cleaning, coating, and inspection operations. For example, previous rotating devices use exposed or external chain and sprocket assemblies or belt and pulley assemblies to transmit torque or rotational motion from a motor to the tubular rotating wheels. During operations, cleaning agents, coating particles, and debris can enter the working components of the prior rotating devices, which can cause excessive wear and tear or a complete cease of the prior tubular rotating devices. Therefore, there is a need for a tubular rotating device, wherein the working or torque transferring portions thereof are enclosed or covered to prevent particles, agents, and other contaminants from contacting such working components.

Embodiments usable within the scope of the present disclosure meet these needs.

SUMMARY

The present disclosure is directed to an apparatus for rotating a plurality of cylindrical members. The apparatus can comprise a plurality of wheels, a plurality of drive gears, a plurality of intermediate gears, and a housing assembly enclosing the plurality of drive gears and the plurality of intermediate gears. Each drive gear of the plurality of drive gears can be connected with a wheel of the plurality of wheels and the plurality of drive gears can be positioned along a generally straight line. Furthermore, each intermediate gear can be positioned between two drive gears of the plurality of drive gears, and the plurality of drive gears and the plurality of intermediate gears can be engaged in a simple gear train configuration. Lastly, the plurality of wheels can be positioned outside of the housing.

In another embodiment of the apparatus for rotating a plurality of cylindrical members, the housing assembly can contain lubricating fluid for reducing friction between the plurality of drive gears and the plurality of intermediate gears. Furthermore, the apparatus can receive one or more cylindrical members thereon, wherein the plurality of wheels can rotate the one or more cylindrical members. In yet another embodiment of the apparatus, the apparatus can receive two or more cylindrical members thereon, wherein the plurality of wheels can rotate the two or more cylindrical members.

The present disclosure is further directed to an apparatus for rotating cylindrical objects. The apparatus can comprise a housing, a first plurality of gears positioned within the housing, a second plurality of gears positioned within the housing. Each gear of the second plurality of gears can be engaged with two gears of the first plurality of gears, and the housing can be adapted to contain gear lubricating fluid therein. The apparatus can further comprise a plurality of wheels positioned externally of the housing and connected with the first plurality of gears. The plurality of wheels can have a diameter that is larger than a height of the housing and can rotate one or more cylindrical objects positioned thereon. In an embodiment of the apparatus for rotating cylindrical objects, the first plurality of gears can be positioned in a generally straight line.

In another embodiment of the apparatus for rotating cylindrical objects, the apparatus can comprise an input gear positioned within the housing, wherein the input gear can be adapted to receive torque from a motor or a gearbox, and wherein the motor can rotate the plurality of wheels. Furthermore, each gear of the first plurality of gears can be connected with two wheels of the plurality of wheels, and each of the two wheels can be positioned on opposite sides of each gear of the first plurality of gears. Also, a diameter of each wheel of the plurality of wheels can be larger than a distance between adjacent gears of the second plurality of gears. Lastly, the first plurality of gears can comprise three or more gears and the plurality of wheels can comprise three or more wheels.

The present disclosure is further directed to a method of rotating a plurality of cylindrical members. The method comprises the steps of providing a first plurality of gears enclosed in a housing, providing a plurality of wheels positioned in line, placing each cylindrical member of the plurality of cylindrical members between adjacent wheels of the plurality of wheels, and rotating the first plurality of gears to rotate the plurality of wheels in a same direction, whereby the plurality of wheels can rotate the plurality of cylindrical members. Furthermore, each wheel of the plurality of wheels can have an axis of rotation, wherein each axis of rotation can be parallel to an adjacent axis of rotation. Lastly, the plurality of wheels can be connected with the first plurality of gears.

In another embodiment of the method, the step of rotating the first plurality of gears, to rotate the plurality of wheels, can comprise connecting a motor to at least one gear of the plurality of gears, or to an additional gear, and powering the motor to rotate the first plurality of gears, whereby rotating the plurality of gears rotates the plurality of wheels.

In yet another embodiment of the method, the step of placing each cylindrical member of the plurality of cylindrical members between adjacent wheels of the plurality of wheels comprises placing each cylindrical member of the plurality of cylindrical members in a wedge shaped space between two adjacent wheels of the plurality of wheels.

The foregoing is intended to give a general idea of the invention, and is not intended to fully define nor limit the invention. The invention will be more fully understood and better appreciated by reference to the following description and drawings.

BRIEF DESCRIPTION OF THE DRAWINGS

In the detailed description of various embodiments usable within the scope of the present disclosure, presented below, reference is made to the accompanying drawings, in which.

One or more embodiments are described below with reference to the listed Figures.

DETAILED DESCRIPTION OF THE EMBODIMENTS

Before describing selected embodiments of the present disclosure in detail, it is to be understood that the present invention is not limited to the particular embodiments described herein. The disclosure and description herein is illustrative and explanatory of one or more presently preferred embodiments and variations thereof, and it will be appreciated by those skilled in the art that various changes in the design, organization, means of operation, structures and location, methodology, and use of mechanical equivalents may be made without departing from the spirit of the invention.

As well, it should be understood that the drawings are intended to illustrate and plainly disclose presently preferred embodiments to one of skill in the art, but are not intended to be manufacturing level drawings or renditions of final products and may include simplified conceptual views to facilitate understanding or explanation. As well, the relative size and arrangement of the components may differ from that shown and still operate within the spirit of the invention.

Moreover, it will be understood that various directions such as "upper", "lower", "bottom", "top", "left", "right", "first", "second" and so forth are made only with respect to explanation in conjunction with the drawings, and that components may be oriented differently, for instance, during transportation and manufacturing as well as operation. Because many varying and different embodiments may be made within the scope of the concept(s) herein taught, and because many modifications may be made in the embodiments described herein, it is to be understood that the details herein are to be interpreted as illustrative and non-limiting.

Figure 1:
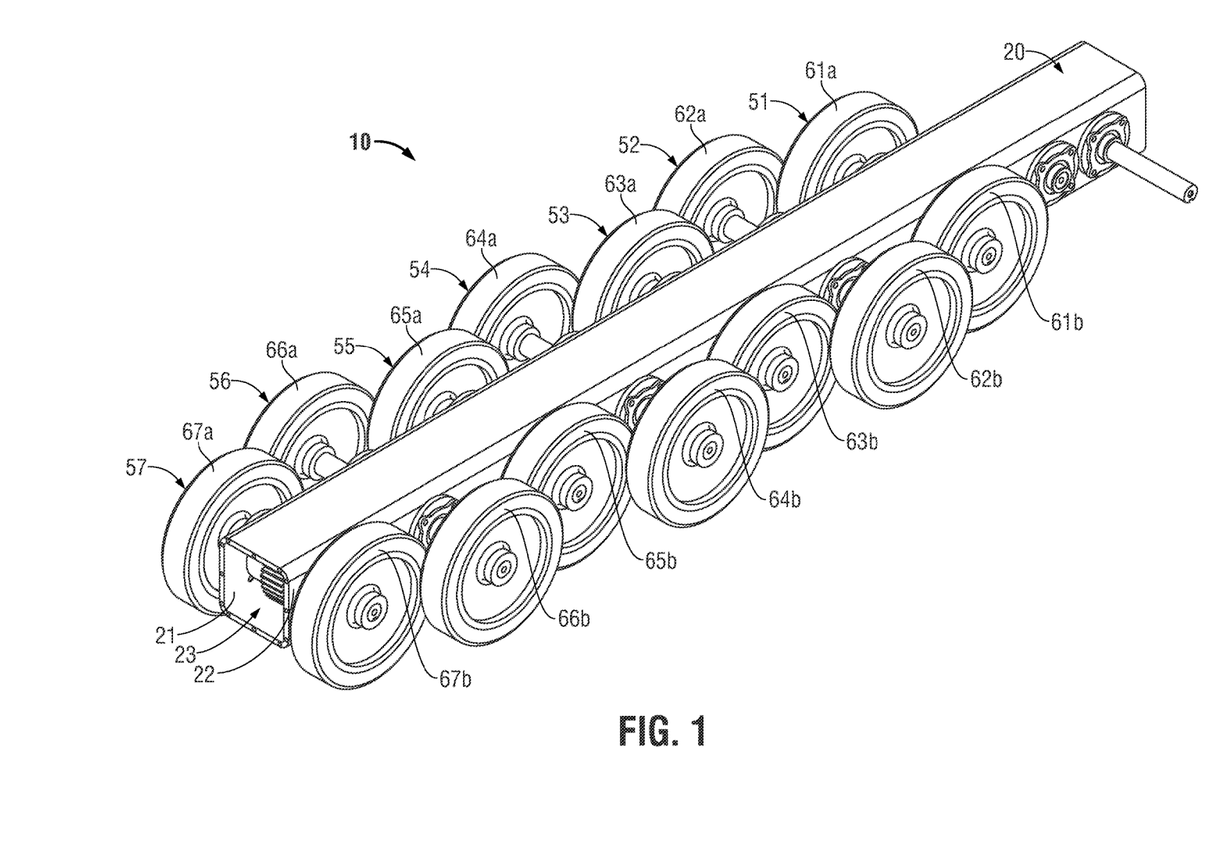
FIG. 1 depicts an isometric view of an embodiment of an apparatus for rotating cylindrical members, in accordance with the present disclosure.

Referring now to FIG. 1, the Figures shows an isometric view of an embodiment of an apparatus for rotating tubulars and other cylindrical members, in accordance with the present disclosure, hereinafter referred to as a rotating apparatus (10). The rotating apparatus (10) is shown comprising a housing (20) with side walls (21) and (22), which maintains seven sets of rotating subassemblies (51-57) in position. The housing (20) is shown having a generally straight and elongated configuration, wherein portions of the rotating subassemblies (51-57) are positioned within the housing (20) and portions of the rotating subassemblies (51-57) are positioned outside of the housing (20). Specifically, the rotating wheels (61a-67a, 61b-67b) of each rotating subassembly (51-57) are shown positioned outside of the housing (20), on opposite sides of the housing (20).

Figure 2:
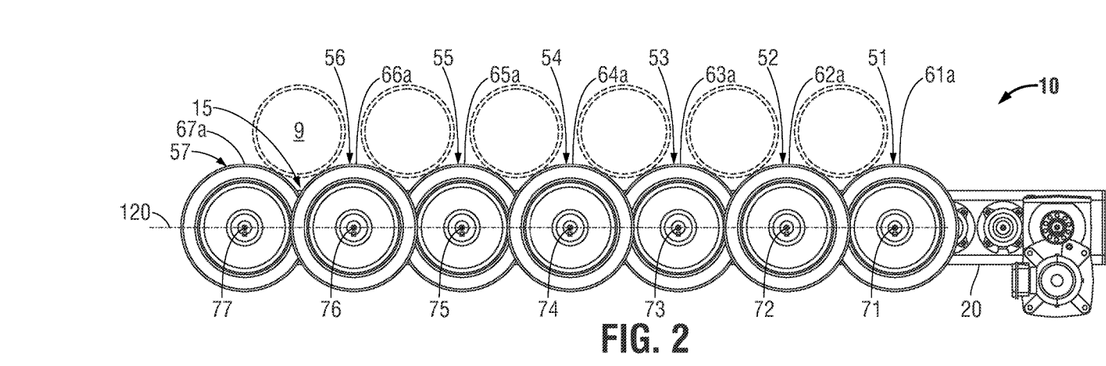
FIG. 2 depicts a side elevational view of an embodiment of an apparatus for rotating cylindrical members, in accordance with the present disclosure.
Figure 3:
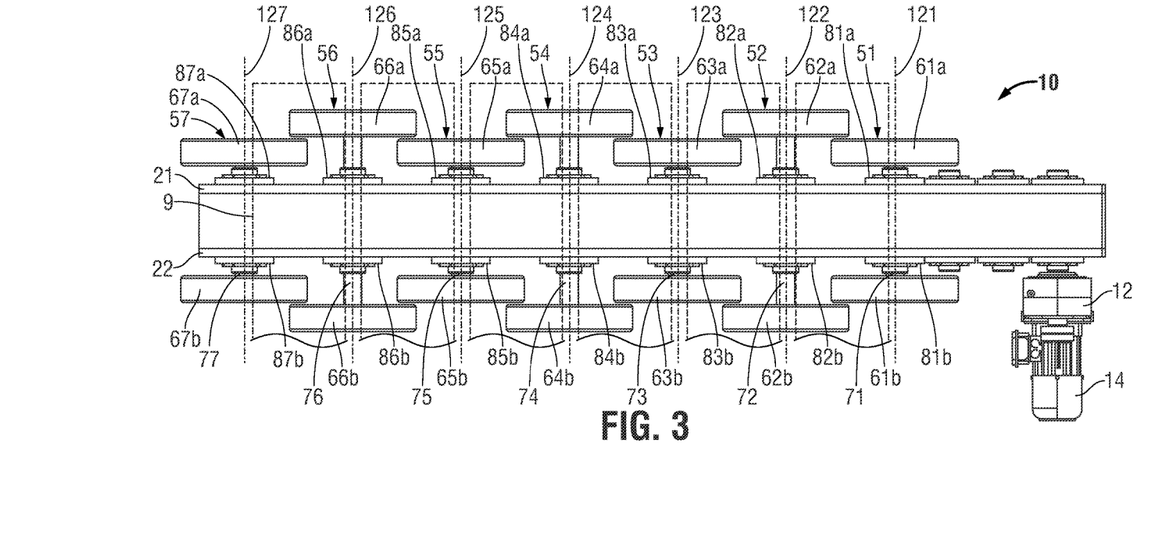
FIG. 3 depicts a top view of an embodiment of an apparatus for rotating cylindrical members, in accordance with the present disclosure.

Referring now to FIGS. 2 and 3, showing a side elevational view and a top view of an embodiment of the rotating apparatus (10), in accordance with the present disclosure. Specifically, FIGS. 2 and 3 show seven sets of rotating subassemblies (51-57) positioned in line (120) along the housing (20). Each rotating subassembly (51-57) is further depicted comprising shafts connecting the wheels (61-67a, 61-67b) to the internal components (see FIGS. 4 & 5) of the rotating subassemblies (51-57). The wheels (61a-67a, 61b-67b) can comprise a diameter larger than the distance between each shaft (71-77), which can result in the wheels (61a-67a, 61b-67b) being positioned to overlap along the length of the housing (20). In order for the wheels (61a-67a, 61b-67b) to overlap, every other rotating subassembly (51-57) can comprise a longer or a shorter shaft, wherein shafts (71, 73, 75, 77) are shorter than shafts (72, 74, 76). Such a configuration results in wheels (62a, 62b, 64a, 64b, 66a, 66b) being located farther away from the housing (20) than wheels (61a, 61b, 63a, 63b, 65a, 65b, 67a, 67b).

The wheels (61a-67a, 61b-67b) can be retained on the support shafts (71-76) by any means known in the art, including threads, splines, or a key. Furthermore, the wheels (61a-67a, 61b-67b) can be sized and spaced from each other to enable tubulars (9) to be placed in the wedge-shaped spaces (15) formed between each wheel (61a-67a, 61b-67b), whereby the rotating action of the wheels can rotate the tubulars (9) in the same direction during various operations. FIG. 3 further depicts each wheel (61a-67a, 61b-67b) having an axis of rotation (121-127). As further depicted in FIG. 2, the diameter of each wheel (61a-67a) can be larger than the height of the housing (20), allowing tubulars (9) to be retained within the wedge-shaped spaces (15) without making contact with the housing (20).

FIGS. 1 and 2 depict the wheels (61a-67a, 61b-67b) having a solid rim or internal portion and an outer diameter portion comprising a non-slip material adapted for creating friction between the wheels (61a-67a, 61b-67b) and the tubulars (9) during operations. The non-slip material can be corrosion and temperature resistant, as certain cleaning or coating elements can be corrosive, and certain operational steps may require the tubulars (9) to be heated during cleaning or coating operations. In other embodiments (not shown) of the coating apparatus (10), the wheels can comprise any configuration known in the art, including a unitary construction, comprising a single plate without additional non-slip material thereon.

Referring to FIG. 3, each shaft (71-77) is shown supported by two radial bearing assemblies positioned about each shaft (71-77) on opposite sides of the housing (20). The radial bearing assemblies (81a-87a, 81b-87b), can allow the shafts (71-77) to rotate within the housing (20) by reducing friction with the walls (21, 22) of the housing (20). The radial bearing assemblies (81a-87a, 81b-87b) can comprise internal ball bearings, roller bearings, metal-to-metal bearings, or any other configuration known in the art, to support the shafts (71-77) during rotating operations. The radial bearing assemblies (81a-87a, 81b-87b) also can comprise fluid sealing means, wherein the bearing assemblies can prevent fluids from escaping from the internal portion of the housing (20) into the external environment. The radial bearing assemblies (81a-87a, 81b-87b) can be further configured to prevent contaminants from entering the internal portion of the housing (20) from the external environment.

Figure 5:
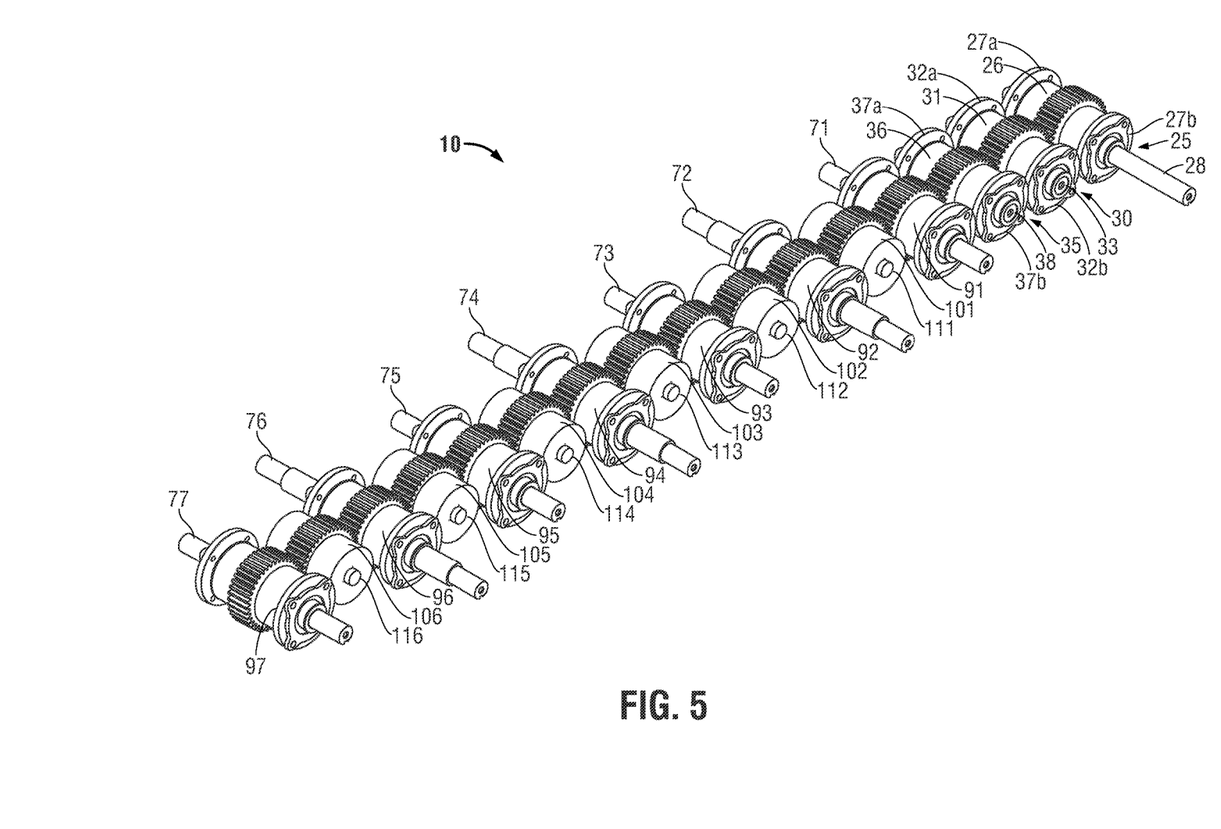
FIG. 5 depicts an isometric view of an embodiment of an apparatus for rotating cylindrical members without the housing and the wheels, in accordance with the present disclosure.

FIGS. 2 and 3 further depict the first end of the rotating apparatus (10) comprising a gear box (12) and an electrical motor (14). The electrical motor (14) can be indirectly connected to the housing ((20), as shown in FIG. 1) and the input shaft ((28), as shown in FIG. 5) by an intermediate gearbox (12), which can connect with the input shaft (28) and the housing (20). The gearbox (12) can reduce the output speed of the motor (14), while increasing the output torque transmitted to the input shaft (28) to enable the rotation of the rotating subassemblies (51-57), and therefore, the tubulars (9) positioned thereon.

Figure 4:
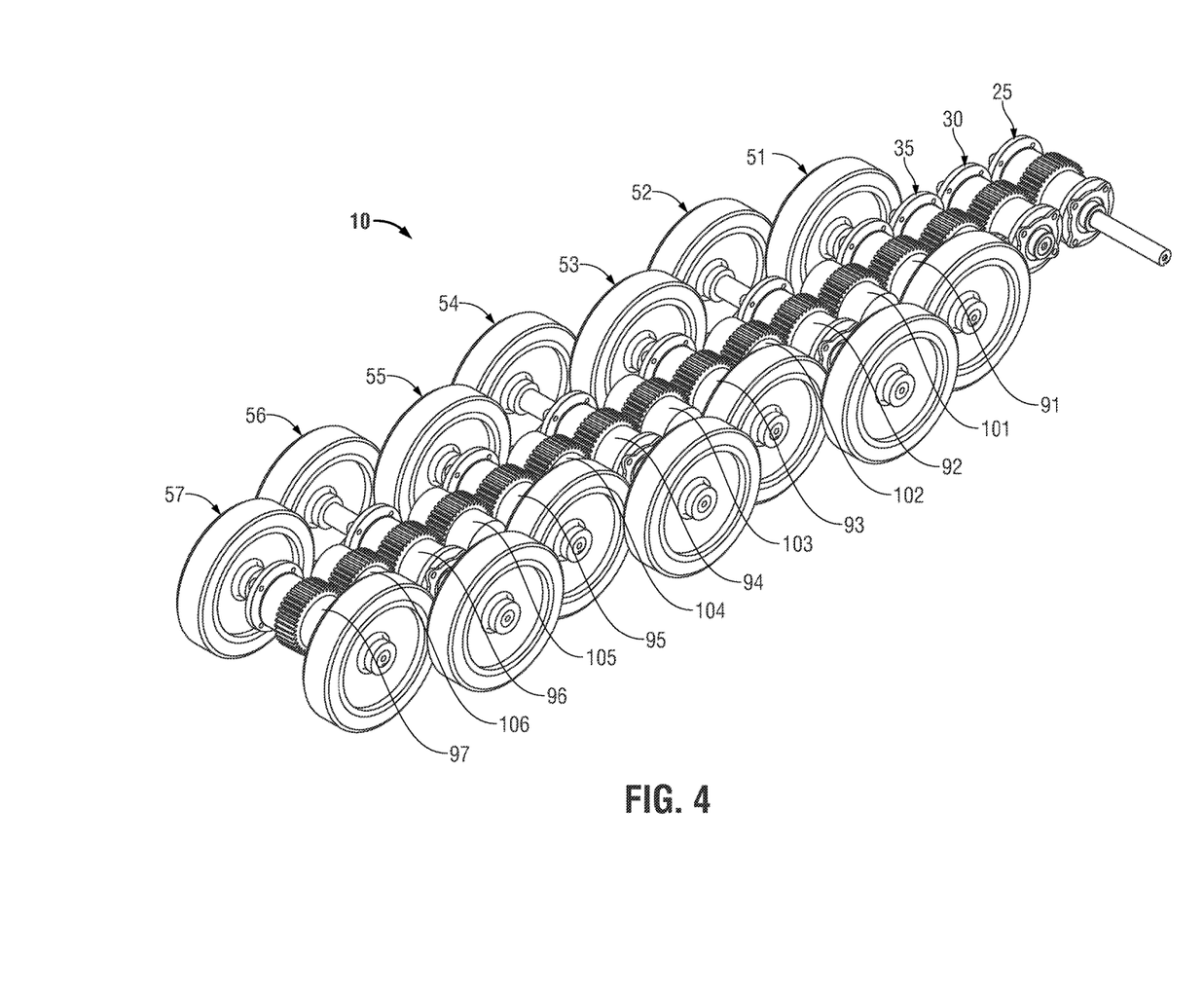
FIG. 4 depicts an isometric view of an embodiment of an apparatus for rotating cylindrical members without the housing, in accordance with the present disclosure.

Referring now to FIGS. 4 and 5, depicting isometric views of the rotating apparatus (10) without the housing (20), for clarity. FIG. 5 further omits the wheels (61a-67a, 61b-67b), for additional clarity. The Figures depict a plurality of gears (26, 31, 36, 91-97, 101-106) connected or engaged in a simple gear train configuration, wherein the gears can be maintained in position by the housing (20). Each gear (26, 31, 36, 91-97, 101-106) is depicted comprising a cylindrical body extending between the side walls (21, 22) of the housing (20) to retain the gears centered within the housing (20). Further, a central portion of each gear (26, 31, 36, 91-97, 101-106) can comprise matching teeth along the circumference of the cylindrical body, allowing the gears to mesh with each other in order to transmit torque.

The gear train is shown comprising seven drive gears (91-97) (i.e., first plurality of gears), three of which have long support shafts (72, 74, 76) extending therethrough and four of which have short support shafts (71, 73, 75, 77) extending therethrough. It should be noted that the seven drive gears (91-97) are part of the seven rotating subassemblies (51-57) previously described. The support shafts (71-76) and the drive gears (91-97) can be attached in order to transfer torque and rotational motion from the drive gears (91-97) to the rotating wheels (61a-67a, 61b-67b). In an embodiment of the rotating apparatus (10), the central portions of the support shafts (71-76) can comprise radial splines (not shown) which can engage corresponding female splines (not shows) in the drive gears (91-97), to prevent relative rotation therebetween. In other embodiments (not shown) of the rotating apparatus (10), the drive gears (91-97) and the shafts (71-76) can be engaged to each other using a threaded connection, welding, crimping, forced or interference fit, one or more fasteners, a keyway and key connection, or by using any other means of attachment that prevents rotation and allows the transfer of torque therebetween. In yet another embodiment (not shown) of the rotating apparatus (10), the drive gears (91-97) and the shafts (71-76) can be integrally formed.

FIGS. 4 and 5 further depict six intermediate gears (101-106) (i.e., second plurality of gears), with each intermediate gear positioned between adjacent drive gears (91-97). In order for each set of rotating wheels (61a-67a, 61b-67b) to rotate in the same direction, intermediate gears (101-106) can be included between the drive gears (91-97), resulting in each set of rotating wheels (61a-67a, 61b-67b) being actuated to rotate in the same direction. As further depicted, each of the intermediate gears (101-106) comprises a support shaft (111-116), which allows each intermediate gear to maintain position and rotate within the housing (20). Unlike the shafts (71-77) of the drive gears (91-97), the shafts (111-116) of the intermediate gears (101-106) do not extend through the side walls (21, 22) of the housing (20), but can protrude into the cavities or channels (not shown) extending longitudinally along the side walls (21, 22) of the housing (20). It should be noted that in other embodiments (not shown) of the rotating apparatus (10), the shafts (111-116) of the intermediate gears (101-106) can have a similar configuration to shafts (71-77), extending through the side walls (21, 22) of the housing (20).

FIGS. 4 and 5 further depict an input gear assembly (25) positioned at the first end of the rotating apparatus (10), wherein the input gear assembly (25) comprises an input gear (26), an input shaft (28) extending through the input gear (26), and first and second radial bearing assemblies (27a, 27b). The input shaft (28) can extend through the walls (21, 22) of the housing (20), wherein one end of the input shaft (28) can be adapted to mate with the gearbox (12) and project farther on one side of the housing (20). The input shaft (28) can be adapted to engage the input gear (26) using any means known in the art to prevent relative rotation and allowing the transfer of torque between the two components, including, but not limited to, welding, crimping, threading, matching splines, and/or keys/locating pins. In yet another embodiment, the input gear (26) and the input shaft (28) can be integrally formed. The radial bearing assemblies (27a, 27b) can comprise the same or similar configuration as the radial bearing assemblies (81a-87a, 81b-87b).

Referring still to FIGS. 4 and 5, two additional gear assemblies (30, 35) are shown positioned between the input gear assembly (25) and the first rotating subassembly (51, see FIG. 3). Each of the additional gear assemblies (30, 35) can comprise an additional gear (31, 36), which engage each other, a first and second radial bearing assemblies (32a, 32b, 37a, 37b), and a support shaft (33, 38), which extends through the additional gear (31, 36) and the housing (20). The radial bearing assemblies (32a, 32b, 37a, 37b) can comprise the same or similar configuration as the radial bearing assemblies (81a-87a, 81b-87b). Generally, the additional gear assemblies (30, 35) can transfer torque from the input gear assembly (25) while creating a space between the input gear assembly (25) and the first rotating subassembly (51) to prevent physical contact or interference between the gear box (12) and the first wheels (61a, 61b). Accordingly, in other embodiments (not shown) of the rotating apparatus (10), the additional gear assemblies (30, 35) may be omitted, if there is not interference between the first wheels (61*a*, 61*b*) and the gearbox (12) and motor (14) assembly.

Although the embodiments of the rotating apparatus (10), depicted in FIGS. 4 and 5, show gears (26, 31, 36, 91-97, 101-106) having a spur (e.g., straight) gear configuration, in other embodiments (not shown) of the rotating apparatus (10), the gears can comprise a helical gear configuration, a screw gear configuration, or any other gear configurations known in the art.

Referring once again to FIGS. 1 and 3, the housing (20) is shown comprising an elongated, single piece construction with a generally square cross-section. Although not shown, the housing can comprise a plurality of holes extending through the first and second walls (21, 22), wherein the holes can receive the plurality of shafts (28, 33, 38, 71-77), therethough, to support the gears (26, 31, 36, 91-97, 101-106) in position, as shown in FIG. 5. In an embodiment of the rotating apparatus (10), the gears (26, 31, 36, 91-97, 101-106), depicted in FIG. 5, can be inserted into the housing (20) through a side opening (23), while the shafts (28, 33, 38, 71-77) can be inserted through the holes (not shown) in the side walls (21, 22) to lock the gears in position. The side walls (21, 22) of the housing (20) can comprise a cavity (not shown) extending partially into each side wall (21, 22) and extending longitudinally along each side wall (21, 22). The cavities can be adapted to receive portions of the support shafts (111-116) that extend beyond each intermediate gear (101-106), to maintain the lateral position of the intermediate gears (101-106). In an embodiment of the rotating apparatus (10), the housing (20) can contain fluid for reducing friction between gears (26, 31, 36, 91-97, 101-106), such as a lubricant, gear oil, or hydraulic fluid. To retain the lubricant in the housing and to prevent contaminants from entering the housing (20), the opening (23) can be enclosed by a cover plate (not shown).

The present disclosure is further directed to a method of rotating tubulars (9), pipe, and other cylindrical members during cleaning, coating, and other operations. During operations, one or more tubulars (9) can be positioned on top of the rotation apparatus (10) to rotate the tubulars (9). As shown in FIGS. 2 and 3, the tubulars (9) can be positioned in the wedge-shaped spaces (15), formed between adjacent wheels (61*a*-67*a*, 61*b*-67*b*), to retain the tubulars in position as the tubulars are rotated. Although FIGS. 2 and 3 depict an embodiment of the rotating apparatus (10) comprising seven sets of wheels (61*a*-67*a*, 61*b*-67*b*), which can rotate up to six tubulars (9), it should be understood that other embodiments (not shown) of the rotating apparatus (10) can comprise a larger or a smaller quantity of rotating subassemblies (51-57), allowing the rotating apparatus (10) to rotate a larger or a smaller quantity of tubulars (9).

Furthermore, in order to increase stability of the tubulars (9) during rotating operations, more than one rotating apparatus (10) may be provided at a distance from the other, to support the tubulars (9) at different positions. Another method of rotating tubulars (9) can comprise the use of a single rotating apparatus (10) to rotate and support the tubulars (9) at a point of contact, while a plurality of freely rotating wheels (not shown), spaced from the rotating apparatus (10), can also be used to support the tubulars (9) at different points of contact. In yet another embodiment (not shown) of the rotating apparatus (10), in order to increase stability of the tubulars (9), each of the support shafts (71-77) can be longer, extending the distance between wheels (61*a*-67*a*) and wheels (61*b*-67*b*).

While various embodiments usable within the scope of the present disclosure have been described with emphasis, it should be understood that within the scope of the appended claims, the present invention can be practiced other than as specifically described herein. It should be understood by persons of ordinary skill in the art that an embodiment of the rotating apparatus (10) in accordance with the present disclosure can comprise all of the elements, features, or method steps described above. However, it should also be understood that each element, feature, or method described above can be incorporated into the rotating apparatus (10) by itself or in combinations, without departing from the scope of the present disclosure.

What is claimed is:

1. An apparatus for rotating a plurality of cylindrical members, the apparatus comprising:
    a plurality of wheels;
    a plurality of drive gears, wherein each drive gear of the plurality of drive gears is connected with two wheels of the plurality of wheels, each of the two wheels is connected on opposite sides of each drive gear, and wherein the plurality of drive gears are positioned along a generally straight line; and
    a housing assembly enclosing the plurality of drive gears, wherein the plurality of wheels is positioned outside of the housing, wherein the apparatus receives two or more cylindrical members thereon, wherein the plurality of wheels rotates the two or more cylindrical members.

2. The apparatus of claim 1, further comprising a plurality of intermediate gears, wherein each intermediate gear is positioned between two drive gears of the plurality of drive gears, wherein the plurality of drive gears and the plurality of intermediate gears are engaged in a simple gear train configuration, wherein the housing assembly encloses the plurality of intermediate gears.

3. The apparatus of claim 1, wherein the diameter of each wheel of the plurality of wheels is larger than a height of the housing assembly.

4. The apparatus of claim 1, wherein a diameter of each wheel of the plurality of wheels is larger than a distance between a shaft of adjacent drive gears of the plurality of drive gears.

5. The apparatus of claim 1, further comprising an input gear positioned within the housing, wherein the input gear is adapted to receive torque from a motor or a gearbox, wherein the motor causes the plurality of wheels to rotate.

6. The apparatus of claim 1, wherein the housing assembly contains lubricating fluid for reducing friction between the plurality of drive gears.

7. The apparatus of claim 1, wherein the apparatus receives one or more cylindrical members thereon, wherein the plurality of wheels rotates the one or more cylindrical members.

8. The apparatus of claim 1, wherein each drive gear of the plurality of drive gears is connected with each wheel of the plurality of wheels by a shaft, wherein each shaft extends through a hole in a wall of the housing.

9. An apparatus for rotating cylindrical objects, the apparatus comprising:
    a housing having a generally straight elongated configuration;
    a first plurality of gears positioned within the housing;
    a second plurality of gears positioned within the housing, wherein each gear of the second plurality of gears is engaged with two gears of the first plurality of gears, wherein the housing is adapted to contain a gear lubricating fluid therein; and a plurality of wheels positioned externally of the housing, wherein the plurality of wheels is connected with the first plurality of gears such that each gear of the first plurality of gears is connected with two wheels of the plurality of wheels, wherein the plurality of wheels comprises a diameter that is larger than a height of the housing, wherein the plurality of wheels rotates one or more cylindrical objects positioned thereon.

10. The apparatus of claim 9, wherein the first plurality of gears are positioned in a generally straight line.

11. The apparatus of claim 9, further comprising an input gear positioned within the housing, wherein the input gear is adapted to receive torque from a motor or a gearbox, wherein the motor rotates the plurality of wheels.

12. The apparatus of claim 10, wherein the plurality of wheels are arranged in a staggered configuration so that some of the wheels are closer to the straight line of the first plurality of gears than others of the wheels.

13. The apparatus of claim 9, wherein each of the two wheels is positioned on opposite sides of each gear of the first plurality of gears.

14. The apparatus of claim 9, wherein a diameter of each wheel of the plurality of wheels is larger than a distance between adjacent gears of the second plurality of gears.

15. The apparatus of claim 9, wherein the first plurality of gears comprises three or more gears, wherein the plurality of wheels comprises three or more wheels.

16. The apparatus of claim 1, wherein the plurality of wheels are arranged in a staggered configuration so that some of the wheels are closer to the straight line of the plurality of drive gears than others of the wheels.

* * * * *